United States Patent [19]

Di Napoli

[11] Patent Number: 5,972,909

[45] Date of Patent: Oct. 26, 1999

[54] USE OF HYALURONIC ACID AND CORRESPONDING SALTS FOR THE PREPARATION OF AN AQUEOUS SOLUTION USEFUL AS INTRA-ARTICULAR LAVAGE LIQUID

[75] Inventor: Guido Di Napoli, Collonge-Bellerive, Switzerland

[73] Assignee: Chemedica S.A., Vouvry, Switzerland

[21] Appl. No.: 09/067,939

[22] Filed: Apr. 28, 1998

[30] Foreign Application Priority Data

Apr. 30, 1997 [IT] Italy .................................. MI97A1014

[51] Int. Cl.$^6$ .................................................. A61K 31/715
[52] U.S. Cl. .................................................. 514/54
[58] Field of Search .................................... 514/54, 825

[56] References Cited

U.S. PATENT DOCUMENTS

| | | | |
|---|---|---|---|
| 4,141,973 | 2/1979 | Balazs | 424/180 |
| 5,409,904 | 4/1995 | Hecht et al. | 514/23 |

FOREIGN PATENT DOCUMENTS

| | | |
|---|---|---|
| 0719559 | 7/1996 | European Pat. Off. . |
| 05279244 | 10/1993 | Japan . |
| 8911857 | 12/1989 | WIPO . |

OTHER PUBLICATIONS

The Journal of Rheumatology, 19:5, pp. 772–779 (1992), "Tidal Irrigation Versus Conservative Medical Management in Patients with Osteoarthritis of the Knee: A Prospective Randomized Study", Robert W. Ike et al.

The Journal of Bone and Joint Surgery, vol. 76–B, No. 3, (May 1994), "The Effect in Vitro of Irrigating Solutions on Intact Rat Articular Cartilage", S. K. Bulstra et al.

*Primary Examiner*—Phyllis G. Spivack
*Attorney, Agent, or Firm*—Hedman, Gibson & Costigan, P.C.

[57] ABSTRACT

Described herein is the use of hyaluronic acid for intra-articular irrigation, in the form of an aqueous solution, comprising hyaluronic acid having molecular weight of between 1.8 and 2.2 million daltons, or one of its pharmaceutically acceptable salts, in a concentration of between approximately 0.1% and approximately 0.9% weight/volume, and one or more cationic species chosen from among sodium, potassium, calcium and magnesium, and one or more anionic species chosen from among chloride ions, phosphate ions and citrate ions.

1 Claim, No Drawings

USE OF HYALURONIC ACID AND CORRESPONDING SALTS FOR THE PREPARATION OF AN AQUEOUS SOLUTION USEFUL AS INTRA-ARTICULAR LAVAGE LIQUID

FIELD OF INVENTION

The present invention refers to the use of hyaluronic acid or its pharmaceutically acceptable salts for the preparation of formulations useful for intra-articular irrigation.

It is well known that in the case of articular lesions of various origin, osteo-arthritis, synovitis, arthroscopic examinations or other diagnostic techniques which act inside the articulation, small fragments of cartilage may detach from the surface of the cartilaginous tissue and remain inside the articulation. In these cases, the patients often feel pain and are affected by articular dysfunctions which are due both to the presence of these fragments and to the deterioration of the surface of the cartilage. In the event of cartilaginous fragments remaining inside the articulation, further damage may occur at the level of the synovial membrane and of the surface of the cartilage. In addition, in the event of acute inflammation of the articulation, often a process of swelling occurs, which is accompanied by pain and articular dysfunction.

STATE OF THE ART

In the above cases, it has proved useful, as an alternative to, or in association with, classic pharmacological treatment by systemic or topical route, to subject the inflamed and/or damaged articulations to lavage with physiologically tolerable solutions.

The intra-articular irrigation technique comprises injecting a lavage liquid in the site of articular action via a first needle, the lavage liquid to act in situ for a variable period of time, generally a few minutes, and allowing the lavage liquid to drain off, possibly by being aspirated through another needle.

Generally, the process is repeated various times in succession, injecting each time small quantities of liquid (in the range of 5–20 ml, and even up to 80 ml of solution) for a total amount of approximately 1–2 liters.

Intra-articular irrigation differs from therapeutic treatment via intra-articular injection of substances having a medical action, not only in the nature, but also in the total volumes of solution injected, which are generally higher, and also for the fact that the lavage liquid is then made to drain off through a drainage needle.

Robert W. Ike et al., in "Tidal Irrigation versus Conservative Medical Management in Patients with Osteo-arthritis of the Knee: A Prospective Randomized Study", The Journal of Rheumatology, 19:5, 772–779, 1992, describe treatment of osteo-arthritis of the knee by means of intra-articular irrigation with saline solution. According to the usual medical practice, a balanced saline solution (BSS) is used as lavage liquid, generally in an overall quantity of 1 or 2 liters.

Bulstra S. K. et al., in "The Journal of Bone and Joint Surgery ", Vol. 76-B, No. 3, May 1994, describe the use of various solutions, such as NaCG 0.9%, Ringer solution, 5% glucose Ringer solution, and Ringer lactate solution, as irrigation liquids during arthroscopy. According to Buistra S. K. et al., the ideal lavage liquid should be compatible at an osmotic level, at the level of the pH, at an ionic level, and have conduction properties. Bulstra et al. report that water by itself has adverse effects on cartilage metabolism, and that the concentration of ions in the saline solution resembles that of serum and other human body fluids, but presents characteristics of acidity (pH 5.3) higher than those of the said fluids and tends to disturb the ionic balance of the cells.

Alongside advantages, such as the removal of fragments of cartilaginous tissue, intra-articular irrigation according to known methods may present drawbacks, such as the production of micro-haemorrhages, especially at the level of the points of injection of the injection or drainage needles; in addition, the use of BSS often proves somewhat harmful for the cartilaginous tissue, given the poor physiological compatibility of this solution with the tissues undergoing treatment.

SUMMARY OF THE INVENTION

The applicant has now found that aqueous solutions containing hyaluronic acid or one of its pharmaceutically acceptable salts can be advantageously utilized in the treatment of articular affections by means of intra-articular irrigation, obtaining results that are unexpectedly superior to those obtainable using BSS. The advantage consists in the fact that the solutions according to the present invention are capable of entrapping fragments to a much higher and more effective degree than BSS. Consequently, it will be possible to obtain the removal even of the smallest fragments, thus considerably reducing the irrigation time, and moreover increasing the effectiveness of the irrigation. In addition, unlike BSS, the solutions that are the object of the present invention can be left in situ, since they are physiologically compatible both with the synovial fluid and with the cartilage and surrounding tissues.

The object of the present invention is therefore the use of hyaluronic acid or one of its pharmaceutically acceptable salts for the preparation of a formulation useful as intra-articular lavage liquid, in the form of an aqueous solution containing hyaluronic acid having molecular weight of between 0.5 and 5.0 million daltons, or one of its pharmaceutically acceptable salts, in a concentration of between approximately 0.1% and 0.9% weight/volume, and preferably comprising moreover one or more cationic species chosen among sodium, potassium, calcium and magnesium, and one or more anionic species, chosen among chloride, phosphate and citrate.

The present aqueous solution is useful in the therapeutic or adjuvant treatment of pathological or traumatic articular dysfunctions, and of articular lesions of various origin and nature, such as rheumatoid arthritis, synovitis, osteo-arthritis, and in particular articular affections of the knee, and in addition as irrigation liquid during arthroscopic examinations or other diagnostic techniques which act inside the articulation. Preferably, the present solution for intra-articular irrigation further contains an antioxidant tolerated by the intra-articular tissues, in particular glucose.

DETAILED DESCRIPTION OF THE INVENTION

Preferred solutions for the purposes of the present invention contain hyaluronic acid or one of its salts, at least one salt selected from calcium salt, magnesium salt, and mixtures thereof, and further one salt of citric acid. Typically, in addition to hyaluronic acid or corresponding salt, they contain sodium, potassium, calcium, magnesium, chloride, and citrate ions.

Typically, the aqueous solutions useful for intra-articular irrigation according to the present invention also contain a phosphate buffer. According to preferred embodiments, they also contain an anti-oxidant tolerated by intra-articular tissues, and in addition a phosphate buffer.

The aqueous solutions useful for the purposes of the present invention contain hyaluronic acid or one of its salts having molecular weight of between 0.5 and 5.0 million daltons, for example of between 1.3 and 2.2 million daltons, at a concentration more preferably of between 0.3% and 0.6% weight/volume, for example of 0.5% weight/volume.

The viscosity of the present solutions is preferably comprised between 30 mPa.sec and 43 mPa.sec., measured at a shear rate of 10 sec$^{-1}$, at 25° C.

For the purposes of the present invention, also hyaluronic acid of a molecular weight different from those given above, but not less than 500,000 daltons, may be used, in concentrations such as to obtain the desired viscosity.

According to a particular embodiment of the present invention, the hyaluronic acid or corresponding salt is the only viscosity-enhancing polymer present in the aqueous solution for intra-articular irrigation according to the present invention.

Typically, sodium hyaluronate (NaHA) is used, or other alkaline or alkaline-earth salts of hyaluronic acid.

The NaHA may be of extractive origin (e.g., from cock's combs or umbilical cords, etc.) or of fermentative origin (e.g., streptococcus, etc.).

The solutions for intra-articular irrigation according to the present invention have moreover the advantage of exhibiting a non-Newtonian rheological behaviour, showing a reduction of viscosity with the increase in the shear stress, even in the presence of salts, such as calcium and/or magnesium salts, and of other substances, such as sodium citrate, sodium ascorbate and/or glucose, and phosphate buffer.

Preferably, the solutions for intra-articular irrigation according to the present invention have a substantially neutral pH, for example of between 7.0 and 7.4.

The phosphate buffer typically contains $HPO_4^-$ ions, typically as sodium or potassium salts, and is preferably added in a sufficient quantity to yield a substantially neutral aqueous solution having the pH above specified.

In addition, the aqueous solutions useful for the purposes of the present invention preferably contain a salt of citric acid (citrate) in a quantity of preferably between 0.7 and 2.5 mmol./liter, more preferably of between 0.7 and 1.6 mmol./liter.

Citrate is typically present as alkali metal salt of citric acid, e.g., trisodium citrate.

As anti-oxidant, glucose is preferred.

In addition to glucose, also other anti-oxidants may be used, and in particular salts of ascorbic acid, either alone or associated together.

Preferably, the solutions for intra-articular irrigation according to the present invention contain glucose (preferably at least 3 mmol./liter). They may optionally contain sodium ascorbate, in a quantity of preferably at least 0.50 mmol./liter.

Preferably, glucose is used as anti-oxidant in quantities of between 3 and 7 mmol./liter, optionally associated with sodium ascorbate, the latter in quantities typically of between 0.50 and 50 mmol./liter, more preferably of between 0.50 and 1.0 mmol./liter.

According to particular embodiments of the present invention, the hyaluronic acid-based solutions may contain one or more, preferably all, of the following components, for which the minimum quantities preferably present are indicated alongside:

sodium: preferably at least 40 mmol./liter, more preferably at least 90 mmol./liter;

potassium: preferably at least 12 mmol./liter, more preferably at least 15 mmol./liter;

calcium: preferably at least 0.4 mmol./liter;

magnesium: preferably at least 0.3 mmol./liter;

chloride: preferably at least 50 mmol./liter, more preferably 100 mmol./liter;

phosphate ions (in particular $HPO_4^{2-}$): preferably at least 6 mmol./liter;

citrate ions: preferably at least 0.7 mmol./liter.

Aqueous solutions further preferred for the purposes of the present invention, in addition to the quantities specified above of hyaluronic acid or of one of its salts, having molecular weight as specified above, contain one or more of the following components, preferably all of them, for which the quantities preferably present are indicated alongside:

$Na^+$: preferably 40–180 mmol./liter, more typically 90–180 mmol./liter;

$K^+$: preferably 12–30 mmol./liter, more typically 15–30 mmol./liter;

$Ca^{++}$: preferably 0.4–0.9 mmol./liter, more typically 0.4–0.8 mmol./liter;

$Mg^{++}$: preferably 0.3–1.00 mmol./liter, more typically 0.3–0.6 mmol./liter;

$Cl^-$: preferably 50–200 mmol./liter, more typically 100–190 mmol./liter;

$HPO_4^{2-}$: preferably 6–12 mmol./liter;

citrate: preferably 0.7–2.5 mmol./liter, more typically 0.7–1.6 mmol./liter.

Preferably, in addition to the above-mentioned components, the solutions useful for the purposes of the present invention contain glucose (preferably 3–7 mmol./liter).

They may also contain sodium ascorbate (preferably 0.50–50 mmol./liter, more typically 0.50–1.00 mmol./liter).

For example, for the purposes of the present invention, sodium hyaluronate-based aqueous solutions may be used as those described in the patent EP-A-719.559, the content of which is herein incorporated by reference, and which describes the use of said solutions as masking fluid for photokeratectomy by means of excimer laser.

The aqueous solutions useful as liquids for intra-articular irrigation according to the present invention are typically sterile, and are prepared mixing the ingredients in water according to conventional methods.

The intra-articular irrigation according to the present invention is, for example, carried out according to the general technique previously described in the present text, with the difference that as lavage liquid a hyaluronic acid-based solution, as described for the purposes of the present invention is used, and with the further difference that the aliquot of solution used for the last irrigation can possibly be left in situ.

The number of intra-articular lavages may vary according to the specific purpose of the treatment and of the seriousness of the lesion to be treated; for example, one or more ravages may be performed, possibly grouped together in cycles.

The hyaluronic acid-based aqueous solution for intra-articular irrigation according to the present invention affords the following advantages with respect to BSS:

it facilitates the entrapping and removal of cartilaginous fragments, thus reducing tissue damage due to the process of aspiration of the lavage liquid in the area of the articulation involved;

it is better tolerated by the articular tissues;

after the irrigation, it may be left in situ, thus facilitating the process of repair of the articular cartilage layer;

it protects the cartilage both against progressive cell-dependent inflammatory decomposition and against destruction of the chondrocytes.

Given below is an example which serves as an illustration of the present invention, without, however, in any way limiting the scope thereof.

EXAMPLE 1

|  | g/100 ml | mmol./liter |
|---|---|---|
| NaHA (MW 1.8–2.2 million daltons) | 0.50 | |
| NaCl | 0.68 | 116 |
| KCl | 0.19 | 26 |
| Na$_2$HPO$_4$.12H$_2$O | 0.33 | 9 |
| Na$_3$.citrate | 0.031 | 1.2 |
| MgCl$_2$.6H$_2$O | 0.009 | 0.45 |
| CaCl$_2$.2H$_2$O | 0.0087 | 0.6 |
| Glucose | 0.09 | 5 |

Methods

We carried out arthroscopy of the knee joint and joint lavage in 10 patients with knee pain and effusion due to trauma who were divided into 2 groups. We performed joint lavage to remove cartilage debris and/or inflammatory cells in both groups of patients. In one group (5 patients) we used BSS (balanced salt solution) under pressure to wash the joints.

At the end of the procedure we removed the BSS from the joint. In the other group (5 patients) we used the composition of Example 1 (the composition) under pressure to wash the joints and left at least 2 ml of the product in the joint at the end of the procedure.

The use of medication which might interfere with the assessment of pain (antidepressants, tranquillizer, etc.) was not permitted during the study. The use of paracetamol was allowed but intake was not allowed for 2 days prior to each assessment.

Primary efficacy criterion was pain on movement (evaluated using the VAS). Knee joint performance using the Lysholm Knee Scoring Scale (LKSS) (scoring scale Am. J. Sports Med. 1982; 10: 150–154) was also assessed.

Secondary parameters were: joint circumference, analgesic consumption, patient and investigator judgement at the end of the study.

Results

1) The composition was well tolerated by the joint tissues during and after joint lavage. No adverse events due to the composition were observed or reported. There were no changes in the laboratory safety parameters.

2) During joint lavage, the composition facilitated the removal of cartilaginous debris due to its viscous nature.

3) The composition was left in the joint after lavage. In the composition group, patients experienced less pain and increased joint function at Week 2 compared to baseline values and to the comparative BSS group. Pain decreased further in the composition group at Weeks 3 and 6 with significant differences compared to baseline and to the control group.

4) The baseline LKSS could not be taken since it was impossible for the patients to undergo this test owing to the severity of the pain. Hence the baseline value was taken as 0. However, from Week 2 onwards, this parameter improved significantly in the composition group compared to baseline and the control group.

5) Joint circumference decreased in the composition group at week 2, 3 and 6 compared to baseline values and to the control group.

| Demographic data | Composition group | BSS group |
|---|---|---|
| No. patients (male) | 5 | 5 |
| Age (years ± S.E.) | 31.5 ± 2.2 | 32.7 ± 1.9 |
| Weight (kg ± S.E.) | 69.6 ± 2.3 | 69.0 ± 2.2 |

| Pain on movement (mm VAS) | Composition group | BSS group |
|---|---|---|
| Baseline (Week 0) | 65.8 ± 11.6 | 63.3 ± 15.9 |
| Week 2 | 35.3 ± 8.9 | 51.9 ± 12.1 |
| Week 3 | 27.4 ± 12.8 | 43.7 ± 9.3 |
| Week 6 | 13.0 ± 9.3 | 27.8 ± 13.2 |

| Lysholm score (mean ± s.d.) | Composition group | BSS group |
|---|---|---|
| Baseline (Week 0) | 0 | 0 |
| Week 2 | 90.3 ± 4.3 | 67.9 ± 15.2 |
| Week 3 | 97.4 ± 3.8 | 76.3 ± 9.3 |
| Week 6 | 98.6 ± 3.7 | 89.8 ± 8.7 |

Conclusions

From the above results we can conclude that the intra-articular joint lavage solution of Example 1 presents the following significant advantages against BSS:

1) The composition facilitates the entrapment and removal of cartilage debris. It also protects the cartilage cells from damage. On the contrary, BSS has been shown to be harmful to cartilage cells.

2) The composition can be left in situ after joint lavage enhancing the repair process of the articular cartilage, decreasing pain and improving joint function. On the other hand, BSS must be removed from the joint.

The dry joint that results is painful and joint movement is restricted.

3) Finally, the composition protects the cartilage from cell-dependent inflammatory process and hence prevents cartilage degradation.

I claim:

1. A therapeutic method for the treatment of articular disfunctions, which comprises subjecting to intra-articular lavage a subject in need of such treatment, by means of an aqueous solution containing:

|  | g/100 ml | mmol./liter |
|---|---|---|
| NaHA (MW 1.8–2.2 million daltons) | 0.50 | |
| NaCl | 0.68 | 116 |
| KCl | 0.19 | 26 |
| Na$_2$HPO$_4$.12H$_2$O | 0.33 | 9 |
| Na$_3$.citrate | 0.031 | 1.2 |
| MgCl$_2$.6H$_2$O | 0.009 | 0.45 |
| CaCl$_2$.2H$_2$O | 0.0087 | 0.6 |
| Glucose | 0.09 | 5 |

* * * * *